United States Patent
Schneider et al.

(10) Patent No.: US 11,655,266 B2
(45) Date of Patent: May 23, 2023

(54) PLATINUM COMPLEXES HAVING BINAPHTHYLDIPHOSPHINE LIGANDS FOR THE CATALYSIS OF THE HYDROXYCARBONYLATION OF ETHYLENICALLY UNSATURATED COMPOUNDS

(71) Applicant: EVONIK OPERATIONS GMBH, Essen (DE)

(72) Inventors: Carolin Schneider, Monheim am Rhein (DE); Ralf Jackstell, Rostock (DE); Matthias Beller, Ostseebad Nienhagen (DE); Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 17/544,254

(22) Filed: Dec. 7, 2021

(65) Prior Publication Data

US 2022/0177506 A1 Jun. 9, 2022

(30) Foreign Application Priority Data

Dec. 9, 2020 (EP) .................................... 20212754

(51) Int. Cl.
  *C07F 15/00* (2006.01)
  *B01J 31/24* (2006.01)
  *C07C 51/14* (2006.01)

(52) U.S. Cl.
  CPC ....... *C07F 15/0093* (2013.01); *B01J 31/2409* (2013.01); *B01J 2231/321* (2013.01); *B01J 2531/828* (2013.01)

(58) Field of Classification Search
  CPC .... C07F 15/0093; B01J 31/2409; C07C 51/14
  See application file for complete search history.

(56) References Cited

U.S. PATENT DOCUMENTS

| 10,167,245 B2 | 1/2019 | Dyballa et al. |
| 2021/0299645 A1 | 9/2021 | Yang et al. |
| 2021/0300957 A1 | 9/2021 | Yang et al. |

FOREIGN PATENT DOCUMENTS

EP  3 388 414 A1  10/2018

OTHER PUBLICATIONS

U.S. Appl. No. 17/544,144, filed Dec. 7, 2021, Schneider et al.
U.S. Appl. No. 17/544,179, filed Dec. 7, 2021, Schneider et al.
U.S. Appl. No. 17/544,227, filed Dec. 7, 2021, Yang et al.
European Search Report dated May 19, 2021 for European Patent Application No. 20212754.4 (5 pages in German with Machine Translation).
Yang, J., et al. A general platinum-catalyzed alkoxycarbonylation of olefins. Chemical Communications. 2020, vol. 56, pp. 5235-5238.

*Primary Examiner* — Sikarl A Witherspoon
(74) *Attorney, Agent, or Firm* — Smith, Gambrell & Russell, LLP

(57) ABSTRACT

Platinum complexes having binaphthyldiphosphine ligands for the catalysis of the hydroxycarbonylation of ethylenically unsaturated compounds.

13 Claims, No Drawings

PLATINUM COMPLEXES HAVING BINAPHTHYLDIPHOSPHINE LIGANDS FOR THE CATALYSIS OF THE HYDROXYCARBONYLATION OF ETHYLENICALLY UNSATURATED COMPOUNDS

Platinum complexes having binaphthyldiphosphine ligands for the catalysis of the hydroxycarbonylation of ethylenically unsaturated compounds The present invention relates to platinum complexes having binaphthyldiphosphine ligands for the catalysis of the hydroxycarbonylation of ethylenically unsaturated compounds.

The hydroxycarbonylation of ethylenically unsaturated compounds is a process of increasing significance. A hydroxycarbonylation is understood to mean the direct reaction of ethylenically unsaturated compounds such as olefins with carbon monoxide in the presence of a metal or a metal complex and a ligand to give the corresponding acids:

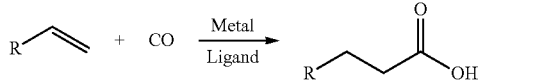

Scheme 1: General reaction equation of the hydroxycarbonylation of an ethylenically unsaturated compound EP 3388414 A1 describes a method of hydroformylation of cyclooctadiene (COD) using 4-([1,1':3',1''-terpheny]-2'-yloxy)-S-dinaphtho[2,1-d:1',2'-f][1,3,2]dioxaphosphepine.

A disadvantage of palladium is its high cost.

The technical problem addressed by the present invention is that of providing novel complexes having a less costly metal than palladium as the central atom. The complexes are additionally to achieve good conversions in hydroxycarbonylations.

This object is achieved by a complex according to claim 1.

Complex comprising Pt and a compound of formula (I)

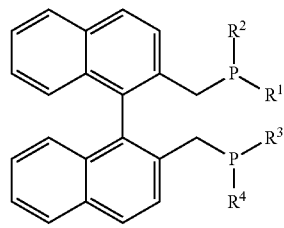

where
$R^1$, $R^2$, $R^3$, $R^4$ are each independently selected from $—(C_1-C_{12})$-alkyl, $—(C_6-C_{20})$-heteroaryl.

The expression $(C_1-C_{12})$-alkyl encompasses straight-chain and branched alkyl groups having 1 to 12 carbon atoms. These are preferably $(C_1-C_8)$-alkyl groups, more preferably $(C_1-C_6)$-alkyl, most preferably $(C_1-C_4)$-alkyl.

The expression $(C_6-C_{20})$-heteroaryl encompasses mono- or polycyclic aromatic hydrocarbyl radicals having 6 to 20 carbon atoms, where one or more of the carbon atoms are replaced by heteroatoms. Preferred heteroatoms are N, O and S. The $(C_6-C_{20})$-heteroaryl groups have 6 to 20, preferably 6 to 14 and more preferably 6 to 10 ring atoms. Thus, for example, pyridyl in the context of this invention is a $C_6$-heteroaryl radical.

Suitable $(C_6-C_{20})$-heteroaryl groups having at least six ring atoms are especially pyridyl, pyridazinyl, pyrimidyl, pyrazinyl, benzofuranyl, indolyl, isoindolyl.

In one embodiment, at least two of the $R^1$, $R^2$, $R^3$, $R^4$ radicals are a $—(C_6-C_{20})$-heteroaryl radical having at least six ring atoms.

In one embodiment, the $R^1$ and $R^3$ radicals are each a $—(C_6-C_{20})$-heteroaryl radical having at least six ring atoms.

In one embodiment, the $R^1$ and $R^3$ radicals are each 2-pyridyl.

In one embodiment, $R^2$ and $R^4$ are $—(C_1-C_{12})$-alkyl.

In one embodiment, $R^2$ and $R^4$ are tert-butyl.

In one embodiment, the compound (I) has the structure (1):

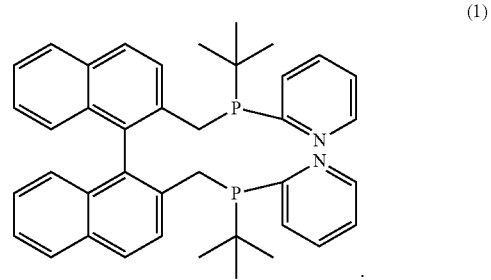 [SMILES: CC(C)(C)P(Cc1ccc2ccccc2c1-c1c(CP(c2ccccn2)C(C)(C)C)ccc2ccccc12)c1ccccn1]

The invention further relates to the use of a complex according to the invention for catalysis of a hydroxycarbonylation reaction.

Process comprising the process steps of:
a) initially charging an ethylenically unsaturated compound;
b) adding a complex as described above, or a compound of formula (I)

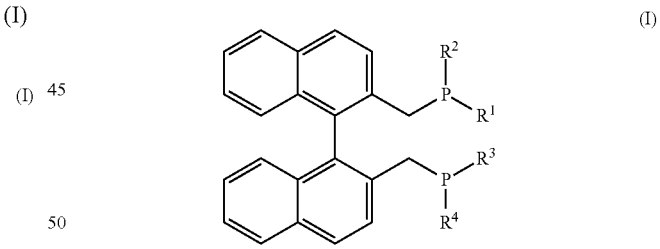

where
$R^1$, $R^2$, $R^3$, $R^4$ are each independently selected from $—(C_1-C_{12})$-alkyl, $—(C_6-C_{20})$-heteroaryl
and
a substance comprising Pt;
c) adding an acid;
d) feeding in CO;
e) heating the reaction mixture from a) to d), with conversion of the ethylenically unsaturated compound to a carboxylic acid.

In this process, process steps a), b), c) and d) can be effected in any desired sequence. Typically, however, the addition of CO is effected after the co-reactants have been initially charged in steps a) to c). In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

In one variant of the process, the ethylenically unsaturated compound does not comprise any further functional groups apart from carbon-carbon double bonds.

In one variant of the process, the ethylenically unsaturated compound is selected from: ethene, propene, 1-butene, cis- and/or trans-2-butene, isobutene, 1,3-butadiene, 1-pentene, cis and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

In one variant of the process, the acid in process step c) is selected from: acetic acid, perchloric acid, sulfuric acid, phosphoric acid, methylphosphonic acid, methanesulfonic acid, trifluoromethanesulfonic acid, tert-butanesulfonic acid, p-toluenesulfonic acid (PTSA), 2-hydroxypropane-2-sulfonic acid, 2,4,6-trimethylbenzenesulfonic acid, dodecylsulfonic acid, camphorsulfonic acid.

In one variant of the process, the acid in process step c) is acetic acid (AcOH).

In one variant of the process, the substance comprising Pt is selected from: platinum dichloride ($PtCl_2$), platinum(II) acetylacetonate [$Pt(acac)_2$], platinum(II) acetate [$Pt(OAc)_2$], dichloro(1,5-cyclooctadiene)platinum(II) [$Pt(cod)_2Cl_2$], bis(dibenzylideneacetone)platinum [$Pt(dba)_2$], bis(acetonitrile) dichloroplatinum(II) [$Pt(CH_3CN)_2Cl_2$], (cinnamyl)platinum dichloride [$Pt(cinnamyl)Cl_2$].

In one variant of the process, the substance comprising Pt is selected from: platinum dichloride ($PtCl_2$), platinum(II) acetylacetonate [$Pt(acac)_2$], platinum(II) acetate [$Pt(OAc)_2$].

CO is fed in in step d) preferably at a partial CO pressure between 0.1 and 10 MPa (1 to 100 bar), preferably between 1 and 8 MPa (10 to 80 bar), more preferably between 2 and 6 MPa (20 to 60 bar).

The reaction mixture is heated in step e) of the process according to the invention preferably to a temperature in the range from 60° C. to 160° C., preferably in the range from 80 to 140° C., more preferably in the range from 80 to 120° C., in order to convert the ethylenically unsaturated compound to an acid.

The invention is to be illustrated in detail hereinafter by a working example.

Conversion of 1-octene to the acid

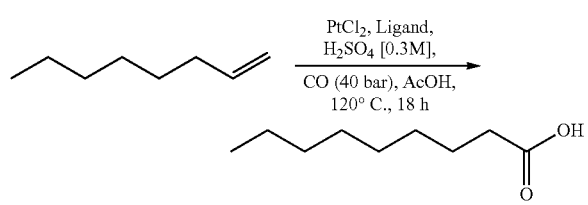

Reaction conditions: 1-octene (1.0 mmol), $PtCl_2$ (0.01 mmol, 1.0 mol %), ligand: bidentate phosphine ligand (0.022 mmol, 2.2 mol %), sulfuric acid [0.3 M] 0.5 ml, AcOH (1.5 ml), pressure (CO): 40 bar, temperature: 120° C., reaction time: 18 h.

The reaction was conducted in a process according to the invention with the ligand (1), and as a comparative experiment with the ligand (2):

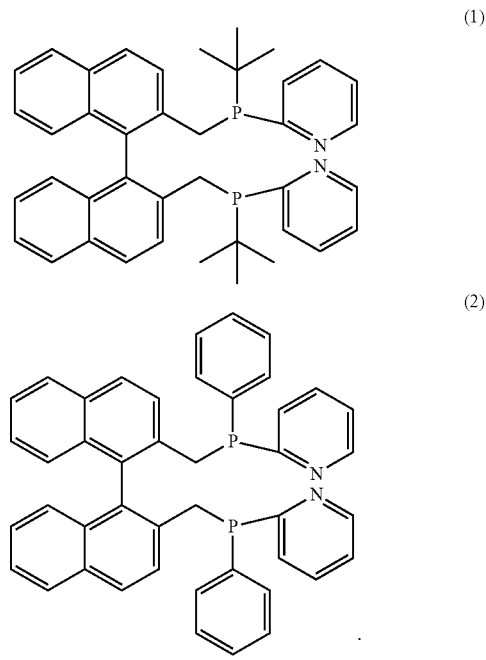

The process according to the invention with ligand (1) gave a yield of 50% here. In the comparative experiment with ligand (2), by contrast, only a yield of 26% was achieved.

The cost of Pt is below that of Pd. The object is thus achieved by a complex according to the invention.

The invention claimed is:
1. Complex comprising Pt and a compound of formula (I)

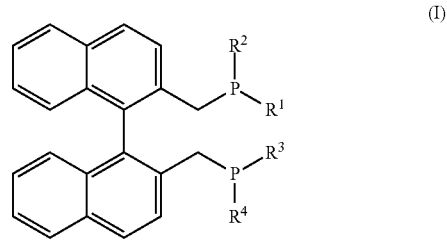

where
$R^1$, $R^2$, $R^3$, $R^4$ are each independently selected from —($C_1$-$C_{12}$)-alkyl, —($C_6$-$C_{20}$)-heteroaryl.

2. Complex according to claim 1,
wherein at least two of the $R^1$, $R^2$, $R^3$, $R^4$ radicals are a —($C_6$-$C_{20}$)-heteroaryl radical having at least six ring atoms.

3. Complex according to claim 1,
wherein the $R^1$ and $R^3$ radicals are each a —($C_6$-$C_{20}$)-heteroaryl radical having at least six ring atoms.

4. Complex according to claim 1,
wherein the $R^1$ and $R^3$ radicals are each 2-pyridyl.

5. Complex according to claim 1,
wherein $R^2$ and $R^4$ are —($C_1$-$C_{12}$)-alkyl.

6. Complex according to claim 1,
wherein $R^2$ and $R^4$ are tert-butyl.

7. Complex according to claim 1,
wherein the compound (I) has the structure (1):

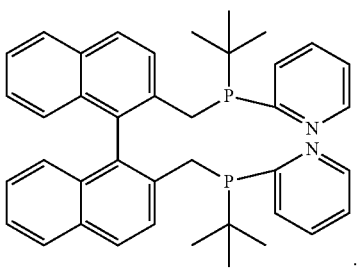

(1)

8. Process comprising the process steps of:
a) initially charging an ethylenically unsaturated compound;
b) adding a complex according to claim 1, or
a compound of formula (I)

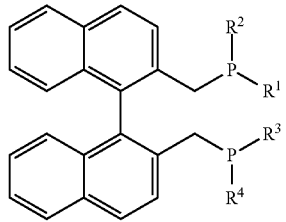

(I)

where
$R^1$, $R^2$, $R^3$, $R^4$ are each independently selected from —($C_1$-$C_{12}$)-alkyl, —($C_6$-$C_{20}$)-heteroaryl
and
a substance comprising Pt;

c) adding an acid;
d) feeding in CO;
e) heating the reaction mixture from a) to d), with conversion of the ethylenically unsaturated compound to a carboxylic acid.

9. Process according to claim 8,
wherein the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

10. Process according to claim 8,
wherein the acid in process step c) is selected from: acetic acid, perchloric acid, sulfuric acid, phosphoric acid, methylphosphonic acid, methanesulfonic acid, trifluoromethanesulfonic acid, tert-butanesulfonic acid, p-toluenesulfonic acid (PTSA), 2-hydroxypropane-2-sulfonic acid, 2,4,6-trimethylbenzenesulfonic acid, dodecylsulfonic acid, camphorsulfonic acid.

11. Process according to claim 8,
wherein the acid in process step c) is acetic acid.

12. Process according to claim 8,
wherein the substance comprising Pt is selected from: platinum dichloride ($PtCl_2$), platinum(II) acetylacetonate [Pt(acac)$_2$], platinum(II) acetate [Pt(OAc)$_2$], dichloro(1,5-cyclooctadiene)platinum(II) [Pt(cod)$_2$Cl$_2$], bis(dibenzylideneacetone)platinum [Pt(dba)$_2$], bis(acetonitrile)dichloroplatinum(II) [Pt(CH$_3$CN)$_2$Cl$_2$], (cinnamyl)platinum dichloride [Pt(cinnamyl)Cl$_2$].

13. Process according to claim 8,
wherein the substance comprising Pt is selected from: platinum dichloride ($PtCl_2$), platinum(II) acetylacetonate [Pt(acac)$_2$], platinum(II) acetate [Pt(OAc)$_2$].

* * * * *